United States Patent [19]
Vinayagamoorthy et al.

[11] Patent Number: 5,711,310
[45] Date of Patent: Jan. 27, 1998

[54] APPARATUS FOR COLLECTING A MID-STREAM URINE SAMPLE

[76] Inventors: Thuraiayah Vinayagamoorthy, 5216 - 14 Avenue, Edmonton, Alberta, Canada, T6L 1Z8; Edmond Charleton, #105, 2841 - 109 Street, Edmonton, Alberta, Canada, T6J 6B7

[21] Appl. No.: 684,661

[22] Filed: Jul. 19, 1996

[51] Int. Cl.$^6$ ........................................ A61B 5/00
[52] U.S. Cl. ............................... 128/760; 604/329
[58] Field of Search ...................... 604/329; 128/762, 128/767, 760; 422/100, 102

[56] References Cited

U.S. PATENT DOCUMENTS

3,894,845 7/1975 McDonald .......................... 23/253 R
3,982,898 9/1976 McDonald .......................... 23/259
4,626,248 12/1986 Scheller ............................. 128/762
4,790,837 12/1988 Gross et al. ....................... 128/762

Primary Examiner—Max Hindenburg
Assistant Examiner—Pamela L. Wingood
Attorney, Agent, or Firm—Anthony R. Lambert

[57] ABSTRACT

An apparatus for collecting a mid-stream urine sample includes a funnel having a wide end and a narrow end. The funnel is supported over a specimen container with the narrow end of the funnel at a mouth of the specimen container. A tubular receptacle depends from and is in fluid communication with the narrow end of the funnel. The tubular receptacle has at least one radial overflow passage adjacent the narrow end of the funnel. Once the tubular receptacle is filled with urine, any further urine entering the tubular receptacle overflows through the radial overflow passage.

9 Claims, 7 Drawing Sheets

APPARATUS FOR COLLECTING A MID-STREAM URINE SAMPLE

FIELD OF THE INVENTION

The present invention relates to an apparatus for collecting a midstream urine sample.

BACKGROUND OF THE INVENTION

It is generally accepted by medical practitioners that urine samples should be taken midstream, as the forestream of urine may be contaminated by micro-organisms. The urethral opening is very close to the anal opening, which is full of micro-organisms. These micro-organisms tend to spread in the pelvic region. It is normal for these micro-organisms to find their way through the urethral opening into the urethra, resulting in contamination of the forestream urine. Midstream urine, which comes from the bladder or the kidney, gives a more accurate indication of whether either the bladder or the kidney are infected by micro-organisms. U.S. Pat. Nos. 3,894,845 and 3,982,898 disclose apparatus for collecting midstream urine samples. These apparatus include a forestream collection and isolation arrangement.

At present patients are asked to provide urine samples in sterile cups with lids. These cups are low cost, disposable items. Although U.S. Pat. Nos. 3,894,845 and 3,982,898 provide a manner of collecting midstream urine samples, they are complex and, consequently, expensive apparatus.

SUMMARY OF THE INVENTION

What is required is a less complex apparatus for collecting a mid-stream urine sample.

According to the present invention there is provided an apparatus for collecting a mid-stream urine sample. A funnel is provided having a wide end and a narrow end. Means is provided for supporting the funnel over a specimen container with the narrow end of the funnel at a mouth of the specimen container. A tubular receptacle depends from and is in fluid communication with the narrow end of the funnel. The tubular receptacle has at least one radial overflow passage adjacent the narrow end of the funnel. Once the tubular receptacle is filled with urine, any further urine entering the tubular receptacle overflows through the at least one radial overflow passage.

With the apparatus, as described above, no urine enters the specimen container until the tubular receptacle has been filled by a forestream. Once the tubular receptacle has been filled, midstream urine overflows from the tubular receptacle into the specimen container. The apparatus is simple enough in construction that it can, if desired, be made disposable along with the specimen container.

Although beneficial results may be obtained through the use of the apparatus, as described above, the size of tubular receptacle that can fit into a disposable cup which is typically used as a specimen container is extremely limited. The tubular receptacle must have sufficient capacity to accommodate the forestream urine, and yet must be of a size that will fit within the specimen container. Even more beneficial results are, therefore, obtained when the tubular receptacle is flexible. The flexible tubular receptacle bends to conform to the liquid receiving cavity of the specimen container. In a small specimen container, the flexible tubular receptacle assumes a "J" shape.

Although beneficial results may be obtained through the use of the apparatus, as described above, air tends to become temporarily trapped by the entry of urine into the specimen container. This air escapes in the form of air bubbles which float up through the urine. Unfortunately, as air bubbles rise to the surface of the urine and burst, an inter-mixing of the forestream urine and the midstream urine can occur. Even more beneficial results may, therefore, be obtained when the tubular receptacle forms a loop with a remote end of the tubular receptacle being in fluid communication with an upper throat of the tubular receptacle. With a loop configuration, the entry of urine forces air out of the remote end of the tubular receptacle. As the remote end of the tubular receptacle is in fluid communication with the upper throat, the air exits without passing through the urine.

Although beneficial results may be obtained through the use of the apparatus, as described above, unless measures are taken to isolate the forestream urine from the midstream urine, it is possible that some intermixing of the forestream and midstream may occur. Even more beneficial results may, therefore, be obtained when a movable valve member is positioned at the remote end of the tubular receptacle. The valve is movable between an open position in the remote end and a closed position projecting from the remote end to block the upper throat. The valve is responsive to liquid pressure such that as urine reaches the remote end of the tubular receptacle the urine exerts pressure upon the valve to move it from the open position to the closed position thereby preventing the entry of further urine into the tubular receptacle.

There are a number of further refinements that can be added to improve the performance of the apparatus described. The presence of air in the specimen container restricts the free entry of liquid into the specimen container. In order to address this problem, it is preferred that the lid have an air release port so that the air can readily be displaced.

The evacuation of air from the tubular receptacle can, similarly, be improved by providing an air evacuation passage that extends from the remote end of the tubular receptacle to the at least one radial overflow passage.

Should the valve member become positioned midway between the open and the closed position, the entry of urine into the tubular receptacle will be restricted. In order to address this problem it is preferred that the valve member have a wedge-like sealing surface. When liquid strikes this wedge-like surface upon entry into the tubular receptacle, it tends to push the valve member back into the open position until a greater liquid pressure is exerted upon the valve member.

An alternative approach to the problem of valve positioning is to provide the remote end of the tubular receptacle with inwardly projecting stops. A weight is then attached to the movable valve member to pull the valve member into the open position resting against the stops, until the biasing force of the weight is overcome by liquid pressure.

There are also alternative valve configurations that can be used. For example, movable valve member can be made of several components. These components can include a liquid responsive plunger positioned in the remote end of the tubular receptacle, a weighted ball valve disposed in the remote end of the tubular receptacle downstream of the liquid responsive plunger and a ball valve seat positioned in the upper throat of the tubular receptacle below a point of intersection with the remote end. With such a configuration, liquid pressure upon the liquid responsive plunger causes the weighted ball valve to be pushed from the remote end of the tubular receptacle falling onto the ball valve seat.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
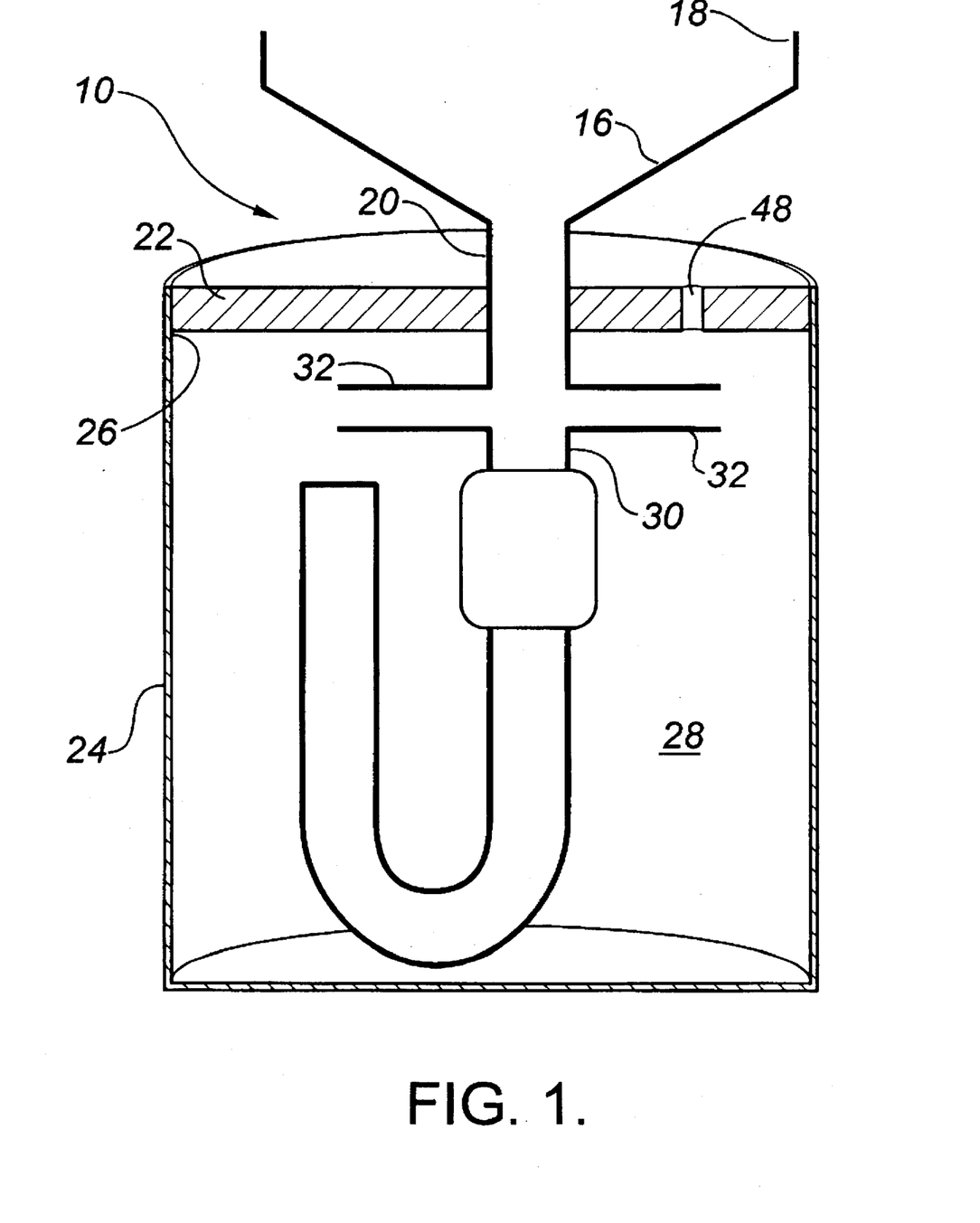
FIG. 1 is a side elevation, in section, of a first embodiment of an apparatus for collecting a midstream urine sample.
Figure 2:
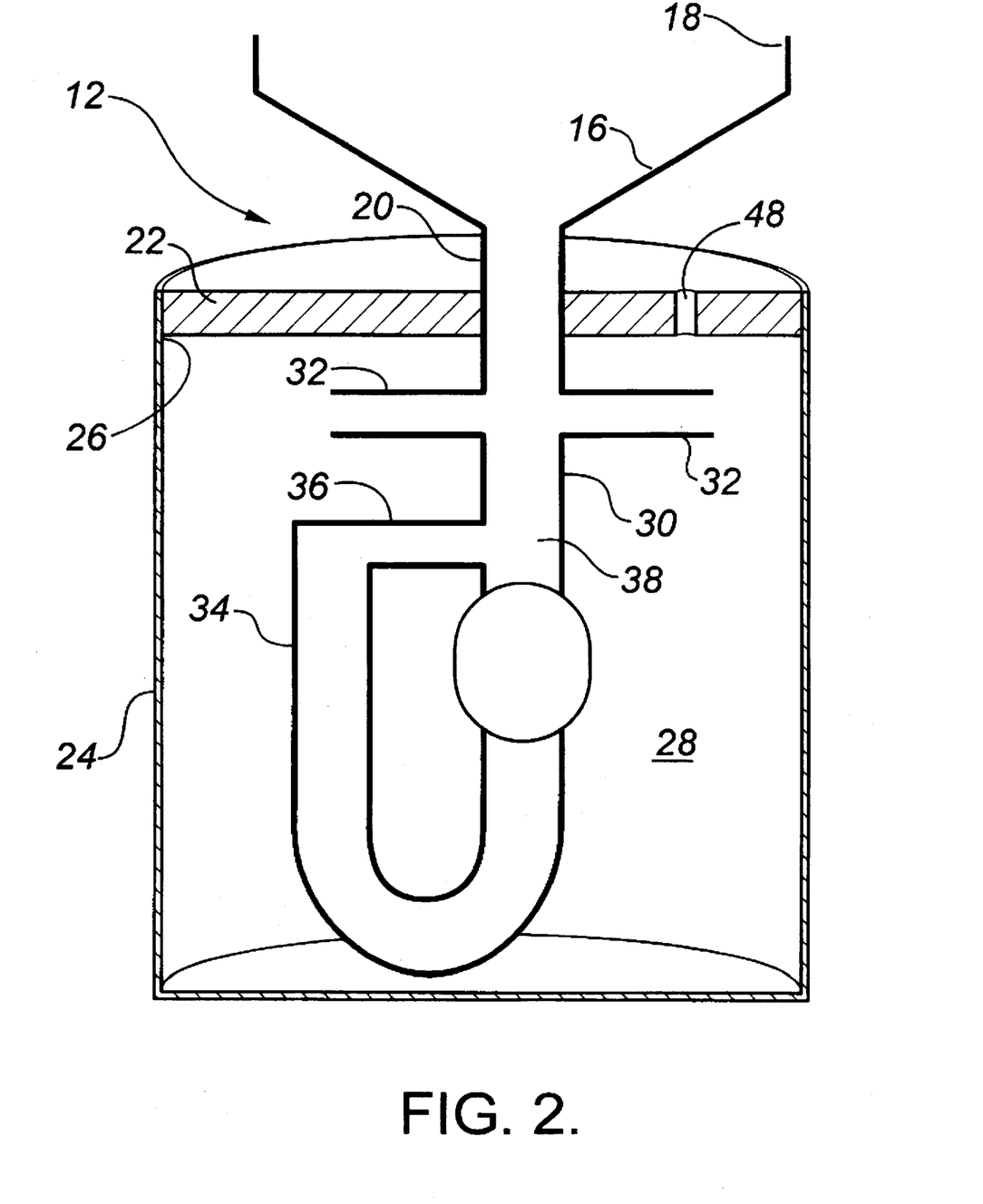
FIG. 2 is a side elevation, in section, of a second embodiment of an apparatus for collecting a midstream urine sample.
Figure 3:
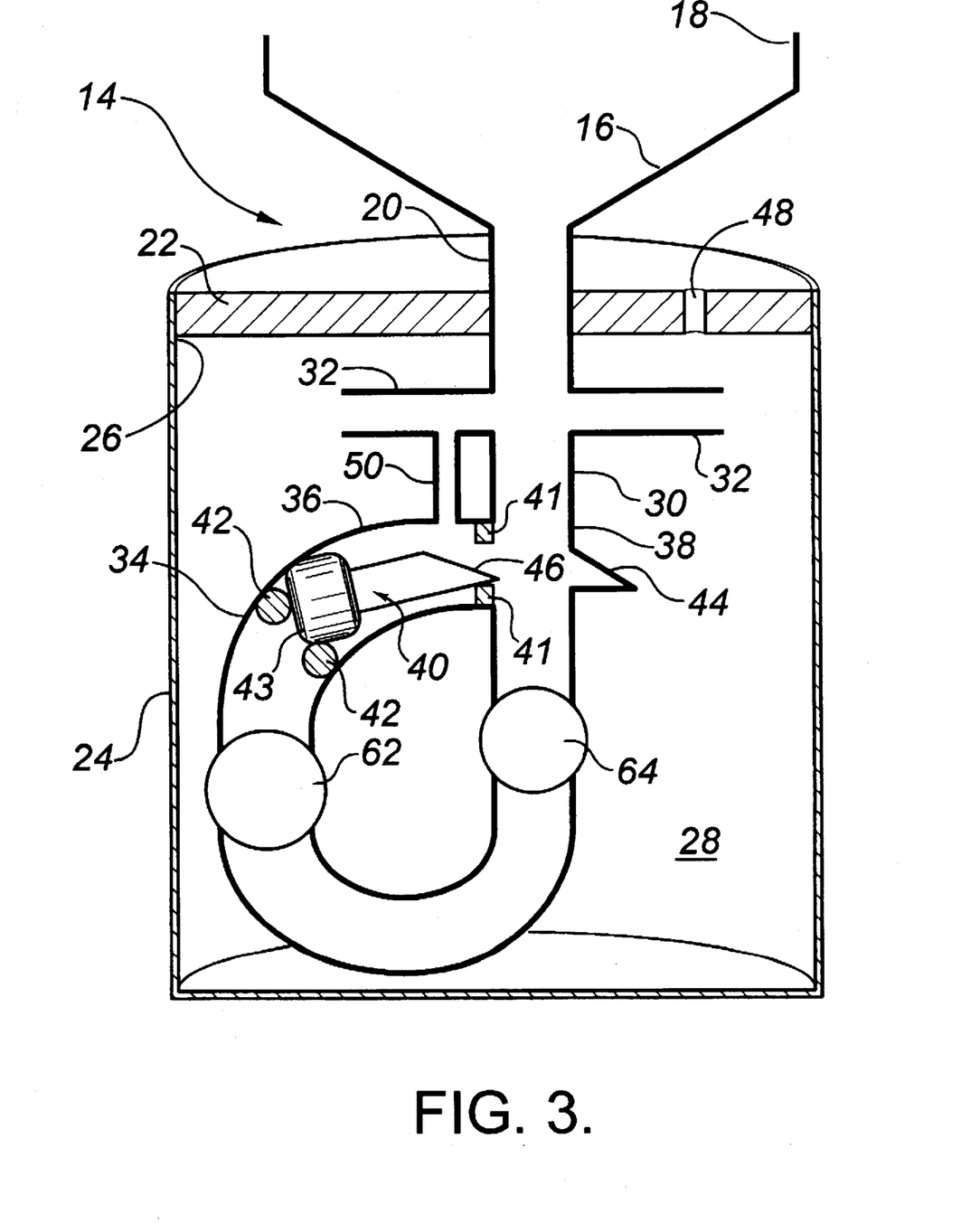
FIG. 3 is a side elevation, in section, of a third embodiment of an apparatus for collecting a midstream urine sample, with a valve member in an open position.
Figure 4:
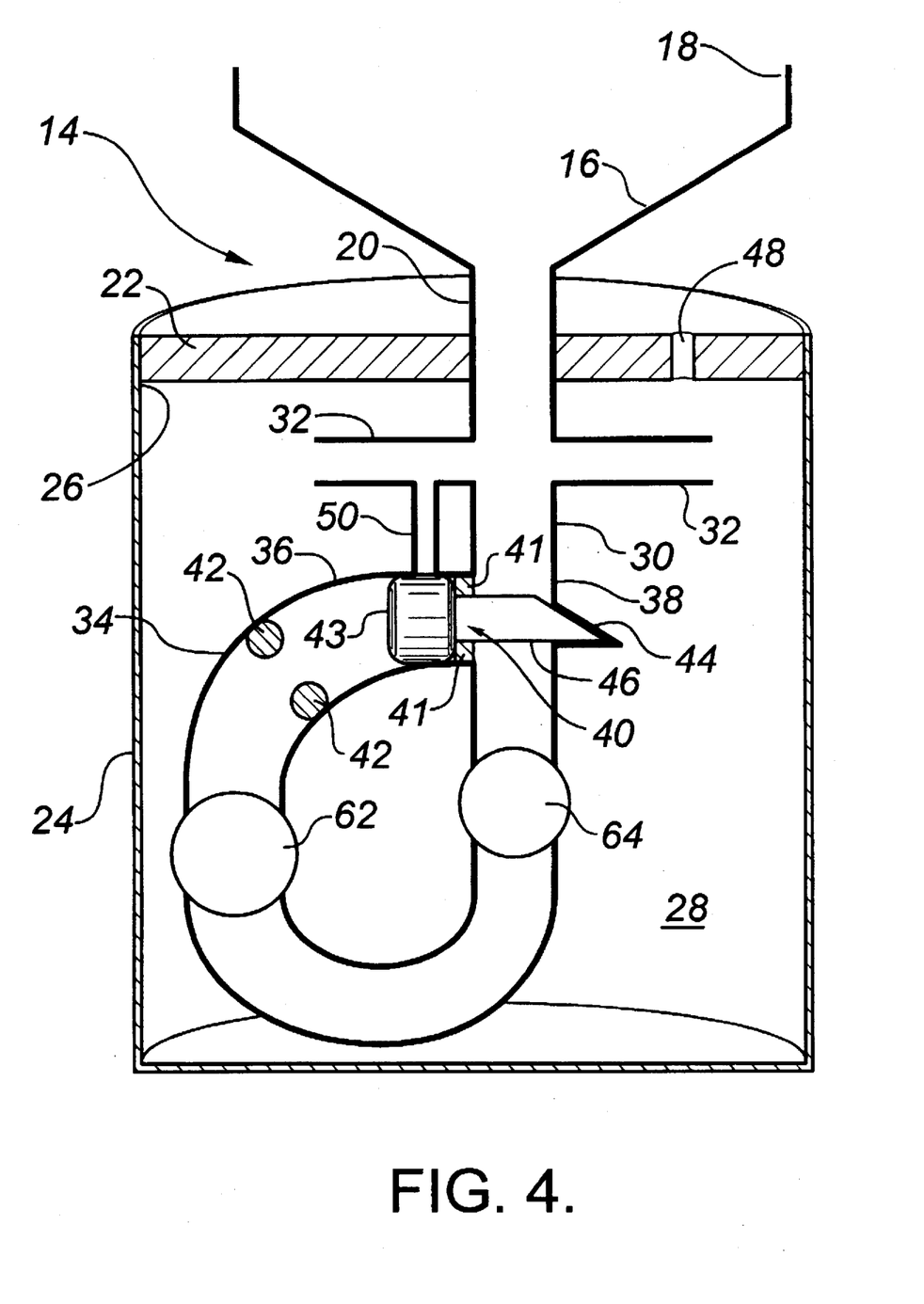
FIG. 4 is a side elevation, in section, of the third embodiment illustrated in FIG. 3, with the valve member in a closed position.

Four preferred embodiments of apparatus for collecting a midstream urine samples, generally identified by reference numerals 10, 12, 14, and 15 respectively, will now be described with reference to FIGS. 1 through 7. First embodiment 10 is illustrated in FIG. 1. Second embodiment 12 is illustrated in FIG. 2. Third embodiment 14 is illustrated in FIGS. 3 and 4, with variations illustrated in FIGS. 5 and 6. Fourth embodiment 15 is illustrated in FIG. 7.

Referring to FIG. 1, first embodiment 10 includes a funnel 16 is provided having a wide end 18 and a narrow end 20. Funnel 16 is incorporated into a lid 22 which fits onto a specimen container 24. As will hereinafter be further described, it is preferred that lid 22 have an air release port 48. Lid 22 when placed onto specimen container 24 serves as the means for supporting funnel 16 over specimen container 24. Lid 22 positions funnel 16 with narrow end 20 at a mouth 26 of a liquid receiving cavity 28 of specimen container 24. A tubular receptacle 30 depends from and is in fluid communication with narrow end 20 of funnel 16. Tubular receptacle 30 has radial overflow passages 32 adjacent narrow end 20 of funnel 16.

The use and operation of first embodiment 10 will now be described with reference to FIG. 1. The lid that normally comes with specimen container 24 is removed and retained for future use. First embodiment 10 is then placed onto specimen container 24, in substitution to the original lid, by positioning lid 22 over mouth 26 of liquid receiving cavity 28. The patient is instructed to urinate into wide end 18 of funnel 16. Urine enters wide end 18 of funnel 16, passing through narrow end 20 and into tubular receptacle 30. Once tubular receptacle 30 is filled with forestream urine, any further urine entering tubular receptacle 30 overflows through radial overflow passages 32 into liquid receiving cavity 28 of specimen container 24. Once the patient has finished providing his urine sample, tubular receptacle 30 containing the forestream urine is disposed of. The lid that comes with specimen container 24 is then used to seal specimen container 24 and the sealed container is forwarded to a laboratory for analysis. It is preferred that tubular receptacle 30 be made of a flexible material. This enables flexible tubular receptacle to bend fit within the dimensions of liquid receiving cavity 28. It will be noted that, in doing so, flexible tubular receptacle 30 assumes a "J" shape.

Referring to FIG. 2, most of the elements of second embodiment 12 are identical to those in first embodiment 10 and have been identified with the same reference numerals. However, second embodiment 12 includes a path by means of which air can escape from tubular receptacle 30. In second embodiment 12, tubular receptacle 30 includes a loop, generally identified by reference numeral 34. Loop 34 is formed by having a remote end 36 of tubular receptacle 30 in fluid communication with an upper throat 38 of tubular receptacle 30.

The use and operation of second embodiment 12 will now be described with reference to FIG. 2. In general the use and operation of second embodiment 12 is identical to that of first embodiment 10. However, with the loop configuration described, the entry of urine forces air out of remote end 36 of tubular receptacle 30. As remote end 36 is in fluid communication with upper throat 38, the air exits from tubular receptacle 30 without having to pass through the accumulated forestream urine. This helps prevent air bubbles from agitating the urine, which could result in an intermixing of some of the forestream urine with the midstream urine entering tubular receptacle 30 and overflowing tubular receptacle 30 overflowing into liquid receiving cavity 28 of specimen container 24 through radial overflow passages 32.

Referring to FIGS. 3 and 4, most of the elements of third embodiment 14 are identical to those in first embodiment 10 and second embodiment 12; they have been identified with the same reference numerals. However, third embodiment 14 includes means for isolating forestream urine from the midstream urine so that no intermixing can possibly occur. A movable valve member 40 is positioned at remote end 36 of tubular receptacle 30. Valve 40 is movable between an open position illustrated in FIG. 3 and a closed position illustrated in FIG. 4. Referring to FIG. 3, in the open position valve member 40 is positioned in remote end 36. Inwardly projecting stops 41 and 42. Stops 41 are forward stops that limit movement in the closed position. Valve member 40 is preferably constructed with an enlarged head portion 43 and an elongate projecting portion 46. Projecting portion 46 fits between forward stops 41. Forward stops 41 perform their intended function by engaging enlarged head portion 43. Stops 42 are rearward stops. They are positioned at remote end 36 of tubular receptacle 30 to prevent valve member 40 from falling into loop 34 when in the open position. They also engage head portion 43. Referring to FIG. 4, in the closed position valve member 40 projects from remote end 36 to block upper throat 38. In order to improve the sealing capability of valve member 40, upper throat 38 has been modified to include a valve seat 44 which receives projecting portion 46 of valve member 40.

The use and operation of third embodiment 14 will now be described with reference to FIGS. 3 and 4. In general, the use and operation of third embodiment 14 is identical to that of second embodiment 12. Although valve member 40 is positioned at remote end 36, air is able to pass by valve member 40 to escape into upper throat 38. Valve member 40 is responsive to liquid pressure. As urine reaches remote end 36 of tubular receptacle 30, the urine exerts pressure upon valve member 40 to move it from the open position, illustrated in FIG. 3, to the closed position, illustrated in FIG. 4. Once valve member 40 is in the closed position, the forestream urine is isolated. Midstream urine entering tubular receptacle 30 overflows into liquid receiving cavity 28 of specimen container 24 through radial overflow passages 32.

Figure 5:
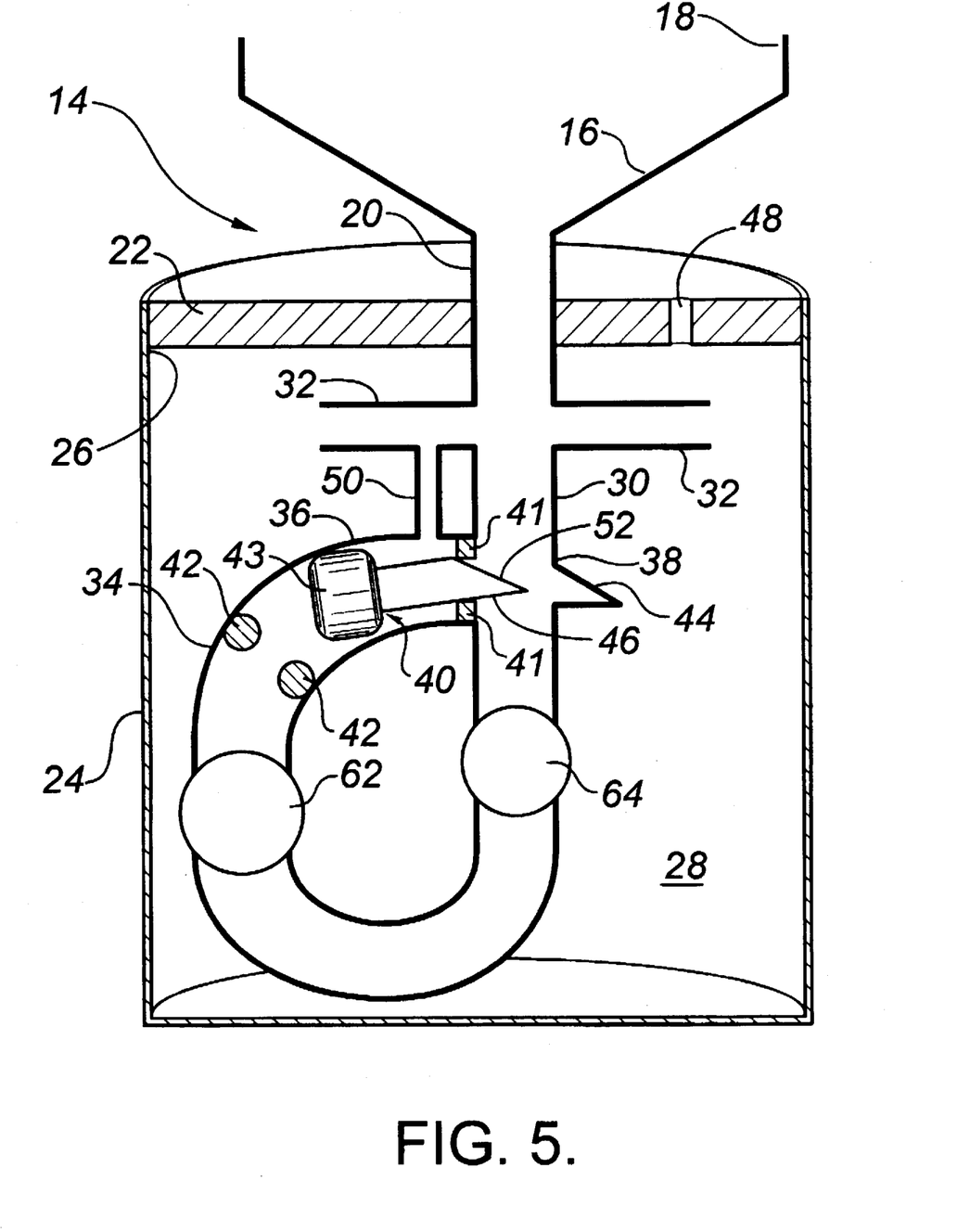
FIG. 5 is a side elevation, in section, of a first modified version of the third embodiment illustrated in FIG. 3.
Figure 6:
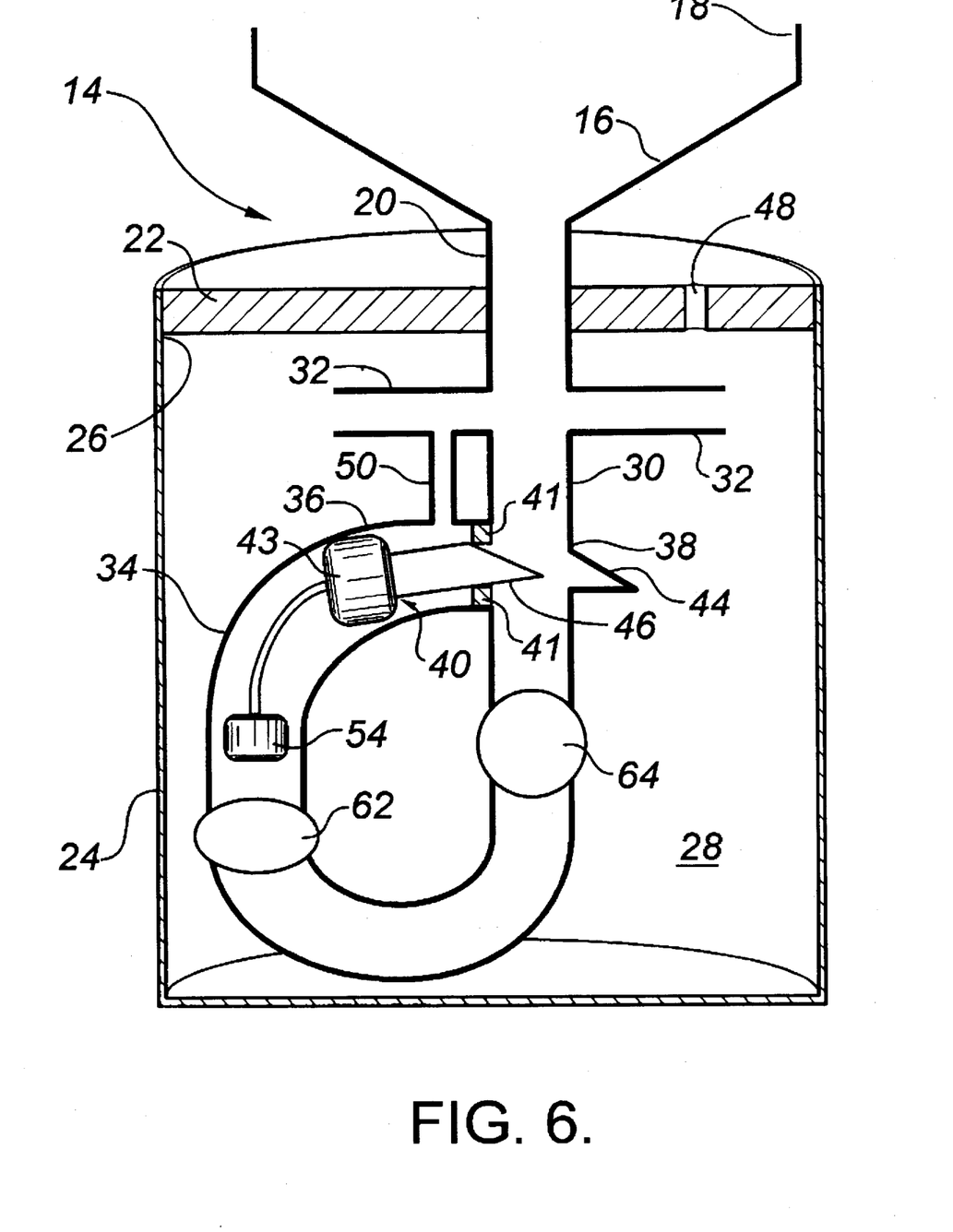
FIG. 6 is a side elevation, in section, of a second modified version of the third embodiment illustrated in FIG. 3.
Figure 7:
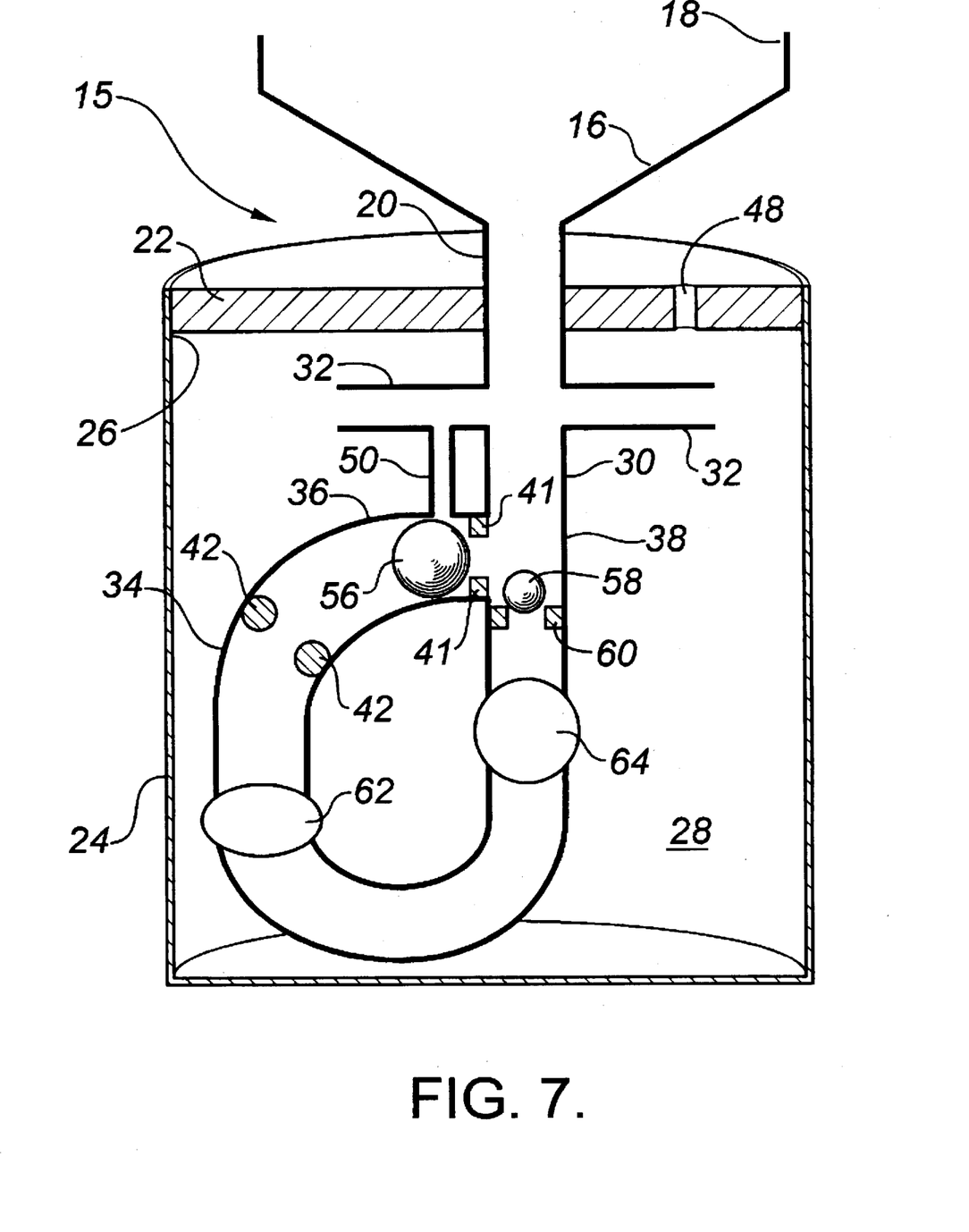
FIG. 7 is a side elevation, in section, of a fourth embodiment of an apparatus for collecting a midstream urine sample, with a modified form of valve member.

Referring to FIGS. 5 and 6, a number of refinements that can be added to improve the performance of third embodiment 14 will now be described. The presence of air in liquid receiving cavity 28 restricts the free entry of liquid into specimen container 24. In order to address this problem, it is preferred that lid 22 have an air release port 48 so that the air can readily be displaced.

The evacuation of air from tubular receptacle 30 can, similarly, be improved by providing an air evacuation passage 50 that extends from remote end 36 of tubular receptacle 30 to one of radial overflow passages 32. It should be noted that air evacuation passage 50 is blocked by valve member 40, when valve member 40 is in the closed position.

Should valve member 40 become positioned midway between the open and the closed position, the entry of urine into tubular receptacle 30 will be restricted. Referring to FIG. 5, in order to address this problem it is preferred that valve member 40 have a wedge-like sealing surface 52. When liquid strikes wedge-like sealing surface 52 upon entry into tubular receptacle 30, it tends to push valve member 40 back into the open position. Eventually, as tubular receptacle fills with urine, sufficient pressure is exerted by the urine upon valve member 40 to push it into the closed position.

Referring to FIG. 6, there is illustrated an alternative approach to the problem of positioning valve member 40. A weight 54 is attached to movable valve member 40 to pull valve member 40 into the open position resting against rearward stops 42. As tubular receptacle 30 becomes filled with urine, the biasing force of weight 54 is overcome by liquid pressure to move valve member 40 into the closed position.

Referring to FIG. 7, there is illustrated an alternative valve configuration 15. In this configuration, movable valve member 40 is made from several interacting components. These components can include a liquid responsive plunger 56, a weighted ball 58 and a ball valve seat 60. Liquid responsive plunger 56 is positioned in remote end 36 of tubular receptacle 30. Weighted ball 58 is disposed in remote end 36 of tubular receptacle 30, downstream of liquid responsive plunger 56. Ball valve seat 60 is positioned in upper throat 38 of tubular receptacle 30 below a point of intersection with remote end 36. With such a configuration, liquid pressure upon liquid responsive plunger 56 causes weighted ball 58 to be pushed from remote end 36 of tubular receptacle 30 falling onto ball valve seat 60. With weighted ball 58 positioned on ball valve seat 60, the forestream urine is isolated from the midstream urine. Forward stops 41 are essential in this application to limit movement of plunger 56.

FIGS. 5 through 7 all illustrate loop 34 with two connective couplings 62 and 64. The purpose of connective couplings 62 and 64 is to enable the size of loop 34 to be expanded as may be required to provide sufficient capacity. Paediatric urine samples are much smaller then adult samples. Hence, the volume of forestream urine that must be captured is much less.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. An apparatus for collecting a mid-stream urine sample, comprising:

a funnel having a wide end and a narrow end;

means for supporting the funnel over a specimen container with the narrow end of the funnel at a mouth of a liquid receiving cavity of the specimen container; and a tubular receptacle depending from and in fluid communication with the narrow end of the funnel, the tubular receptacle having at least one radial overflow passage adjacent the narrow end of the funnel and below the support means, such that once the tubular receptacle is filled with urine, any further urine entering the tubular receptacle overflows through the at least one radial overflow passage, the tubular receptacle forming a loop with a remote end of the tubular receptacle being in fluid communication with an upper throat of the tubular receptacle.

2. The apparatus as defined in claim 1, wherein a movable valve member is positioned at the remote end of the tubular receptacle, the valve being movable between an open position in the remote end and a closed position projecting from the remote end to block the upper throat, the valve being responsive to liquid pressure such that as a urine reaches the remote end of the tubular receptacle the urine exerts pressures upon the valve to move it from the open position to the closed position.

3. The apparatus as defined in claim 2, wherein the valve member has a wedge-like sealing surface.

4. The apparatus as defined in claim 1, wherein the means for supporting the funnel over a specimen container being to secure the funnel to a lid for the specimen container.

5. The apparatus as defined in claim 4, wherein the lid has an air release port.

6. The apparatus as defined in claim 2, the remote end of the tubular receptacle having inwardly projecting stops, and the movable valve member having a depending weight which pulls the valve member into the open position resting against the stops, until the biasing force of the weight is overcome by liquid pressure.

7. The apparatus as defined in claim 1, wherein an air evacuation passage extends from the remote end of the tubular receptacle to the at least one radial overflow passage.

8. An apparatus for collecting a mid-stream urine sample, comprising:

a lid with an aperture;

a funnel having a wide end and a narrow end, the narrow end of the funnel being positioned in the aperture of the lid;

a flexible tubular receptacle depending from and in fluid communication with the narrow end of the funnel, the tubular receptacle having at least one radial overflow passage adjacent the narrow end of the funnel, such that once the tubular receptacle is filled with urine, any further urine entering the tubular receptacle overflows through the at least one radial overflow passage;

the tubular receptacle forming a loop with a remote end of the tubular receptacle being in fluid communication with an upper throat of the tubular receptacle; and a movable valve member positioned at the remote end of the tubular receptacle, the valve being movable between an open position in the remote end and a closed position projecting from the remote end to block the upper throat, the valve being responsive to liquid pressure such that as urine reaches the remote end of the tubular receptacle the urine exerts pressure upon the valve to move it from the open position to the closed position.

9. In combination:

a specimen container having a mouth and a liquid receiving cavity;

a lid with an aperture positioned across the mouth of the specimen container;

a funnel having a wide end and a narrow end, the narrow end of the funnel being positioned in the aperture of the lid;

a flexible tubular receptacle depending from and in fluid communication with the narrow end of the funnel, the tubular receptacle extending into the liquid receiving cavity and bending to conform with the liquid receiving cavity, the tubular receptacle having at least one radial overflow passage adjacent the narrow end of the funnel, such that once the tubular receptacle is filled with urine, any further urine entering the tubular receptacle overflows through the at least one radial overflow passage into the liquid receiving cavity of the specimen container;

the tubular receptacle forming a loop with a remote end of the tubular receptacle being in fluid communication with an upper throat of the tubular receptacle; and a movable valve member positioned at the remote end of the tubular receptacle, the valve being movable between an open position in the remote end and a closed position projecting from the remote end to block the upper throat, the valve being responsive to liquid pressure such that as urine reaches the remote end of the tubular receptacle the urine exerts pressure upon the valve to move it from the open position to the closed position.

\* \* \* \* \*